(12) United States Patent
Naito et al.

(10) Patent No.: US 6,231,890 B1
(45) Date of Patent: May 15, 2001

(54) SUSPENSION OF SPARINGLY WATER-SOLUBLE ACIDIC DRUG

(75) Inventors: Mayumi Naito; Hiroshi Nakano; Kazuo Hasegawa; Toshiaki Nakajima; Ichiro Okudaira; Kenji Tsunoda, all of Tokyo (JP)

(73) Assignee: Taisho Pharmaceutical Co., Ltd. (JP)

( * ) Notice: Subject to any disclaimer, the term of this patent is extended or adjusted under 35 U.S.C. 154(b) by 0 days.

(21) Appl. No.: 09/171,631

(22) PCT Filed: May 1, 1997

(86) PCT No.: PCT/JP97/01496

§ 371 Date: Oct. 22, 1998

§ 102(e) Date: Oct. 22, 1998

(87) PCT Pub. No.: WO97/41832

PCT Pub. Date: Nov. 13, 1997

(30) Foreign Application Priority Data

May 2, 1996 (JP) .................................................... 8-111468

(51) Int. Cl.⁷ .............................. A61K 9/14; A61K 47/00
(52) U.S. Cl. ......................... 424/489; 514/781; 514/785
(58) Field of Search .................................. 424/489, 488, 424/464, 465, 480, 501, 502; 514/781, 785

(56) References Cited

U.S. PATENT DOCUMENTS

| | | | |
|---|---|---|---|
| 4,788,220 | * 11/1988 | Mody et al. | 424/488 |
| 4,975,465 | * 12/1990 | Motola et al. | 514/557 |
| 5,456,920 | * 10/1995 | Matoba et al. | 424/465 |
| 5,731,006 | * 3/1998 | Akiyama et al. | 424/502 |

FOREIGN PATENT DOCUMENTS 405930 1/1991 (EP) .

OTHER PUBLICATIONS

Patent Abstracts of Japan, vol. 1997, No. 4, Apr. 30, 1997 & JP 08 333265.
Patent Abstracts of Japan, vol. 1997, No. 4, Apr. 30, 1997 & JP 08 337524.
Chemical Abstracts of Japan, vol. 101, No. 16, Oct. 15, 1984, #137025 & JP 59 051214.
Patent Abstracts of Japan, vol. 1997, No. 4, Apr. 30, 1997 & JP 08 333246.

* cited by examiner

Primary Examiner—Thurman K. Page
Assistant Examiner—Amy E. Pulliam
(74) Attorney, Agent, or Firm—Lorusso & Loud

(57) ABSTRACT

A suspension of a sparingly water-soluble acidic drug, especially, a nonsteroidal anti-inflammatory analgesic agent, which is stable for a prolonged period of time and is highly dissolvable, and a process for simply and easily producing the suspension. This suspension has a pH value of 2 to 5 and comprises a sparingly water-soluble acidic drug whose average particle size ranges from 1 to 15 $\mu$m, a polyglycerol fatty acid ester, a water-soluble polyhydric alcohol and water, optionally, together with an inorganic powder having an average particle size of 1 to 15 $\mu$m. This process is characterized by carrying out pulverization and dispersion of a sparingly water-soluble acid drug, a polyglycerol fatty acid ester, a water-soluble polyhydric alcohol and water by means of a pulverizer comprising a main shaft adapted to rotate in a casing and a plurality of layshafts adapted to revolve in relationship interlocked with the rotation of the main shaft, each of the layshafts being fitted with a multiplicity of annular griding media.

17 Claims, No Drawings

SUSPENSION OF SPARINGLY WATER-SOLUBLE ACIDIC DRUG

TECHNICAL FIELD

This invention relates to a composition wherein a sparingly water-soluble acidic drug (and an inorganic powder) is/are suspended in the form of fine particles, and a process for the preparation thereof.

BACKGROUND ART

As the liquid preparations of a sparingly water-soluble acidic drug such as a non-steroidal analgesic or anti-inflammatory drug, suspending syrups are disclosed in JP-A-1-258618 and JP-A-2-286615. These syrups, however, have the problem in stability of their suspended particles with lapse of time. More specifically, these publications report that the commercially available suspending liquid preparations preferably have a particle size of 30–250 μm and that particles with a less size undesirably float and those with a larger size precipitate. However, a suspended substance within the disclosed range of particle size precipitates tightly at the bottom of a vessel and thus it should be redispersed by vigorous shaking just before oral administration. However, this redispersion is extremely difficult and even redispersed, there have arisen the problems of an unpleasant rough feeling in the mouth and agglomeration of the drug in the stomach, thus not exerting sufficient effects.

In order to solve the above problems, there may be proposed a means of pulverizing a drug. However, it has been difficult in the processes using conventional apparatuses such as a homogenizer or the like to set up the conditions such as high concentration and viscosity of the drug or stabilizer, a low-temperature control or the like, and the pulverization to the required particle size was difficult to achieve.

Moreover, many of surface active agents or thickeners may dissolve ibuprofen or the like and selection of these suspension-stabilizing components is significant not only for stability of suspended particles but also for irritating property.

Furthermore, many of sparingly water-soluble acidic drugs may melt at or around a sterilization temperature and there have been presented the problems such as diminished ingestiveness due to change in drug properties by a high-temperature sterilization during the preparation.

DISCLOSURE OF THE INVENTION

An object of this invention is to provide a suspension of a sparingly water-soluble acidic drug in which the acidic drug is stable over a prolonged period of time and highly dissolvable and which further can be subjected to a high-temperature sterilization, has a diminished irritative property to the oropharyngeal mucous membrane and is easy to take.

Another object of this invention is to provide a process for simply and easily producing the suspension having superior properties as stated above.

We made our earnest studies to improve dissolution and stability of sparingly water-soluble acidic drugs, especially non-steroidal anti-inflammatory or analgesic agents. As a result, it has been found that in a suspension of a sparingly water-soluble acidic drug having average particle size of 1–15 μm, a polyglycerol fatty acid ester, a water-soluble polyhydric alcohol and water, the acidic drug is stable over a prolonged period of time and highly dissolvable. It has also been found that a high-temperature sterilization can be applied and irritation to the oropharyngeal mucous membrane can be diminished by incorporating into said suspension an inorganic powder having average particle size of 1–15 μm.

More particularly, this invention relates to a suspension of a sparingly water-soluble acidic drug whose average particle size is 1–15 μm, a polyglycerol fatty acid ester, a water-soluble polyhydric alcohol and water, and a suspension of a sparingly water-soluble acidic drug whose average particle size is 1–15 μm, an inorganic powder whose average particle size is 1–15 μm, a polyglycerol fatty acid ester, a water-soluble polyhydric alcohol and water. It is further concerned with a process for the preparation of a suspension of a sparingly water-soluble acidic drug whose average particle size is 1–15 μm, which comprises pulverizing and dispersing a sparingly water-soluble acidic drug, a polyglycerol fatty acid ester, a water-soluble polyhydric alcohol and water by means of a pulverizer comprising a main shaft adapted to rotate in a casing and a plurality of layshafts adapted to revolve in relationship interlocked with the rotation of the main shaft, each of the layshafts being fitted with a multiplicity of annular grinding media.

The sparingly water-soluble acidic drug as used herein is meant to indicate the drug which shows crystallizability at a melting point of around 40–120° C., is sparingly soluble in water in a lower pH range and has an acidic group or a salt thereof, for example, a carboxyl group, a thiocarboxyl group, a dithiocarboxyl group, a sulfo group, a sulfino group, etc. One such drug may be ibuprofen. It is essential that this sparingly water-soluble acidic drug has an average particle size of 1–15 μm. If it is less than this range, irritation by the sparingly water-soluble drug will be enhanced when administered, while, if more than this range, ingestiveness or precipitation stability of suspended particles will become inferior.

An essential surface active agent is a polyglycerol fatty acid ester. Polyoxyethylene sorbitan monooleate surface active agents (Polysolvate 80 and the like) or polyoxyethylene hydrogenated castor oil surface active agents (HCO 60 and the like) are not desirable, because they may increase solubility of ibuprofen or floatings may be generated with lapse of time.

Preferable polyglycerol fatty acid esters may be those in which a polymerization degree of glycerol is 3 or more, the fatty acid has 12–22 carbon atoms, the number of fatty acids bound by ester linkage is 1–7 and the final HLB is not less than 4.

Of these polyglycerol fatty acid esters, preferable ones are decaglycerol monostearate, decaglycerol distearate, heptaglycerol monostearate, decaglycerol heptabehenoate and the like, and they may be used alone or in combination with two or more thereof.

An amount of the polyglycerol fatty acid ester to be incorporated is 0.001–1.0% by weight, preferably 0.002–0.5% by weight, in terms of the final preparation. If it is less than 0.001% by weight, dispersion of suspended particles will be insufficient, while, if more than 1.0% by weight, a solubility of the drug may be increased and irritative property may be strengthened.

As the water-soluble polyhydric alcohol, there may be mentioned, for example, glycerol, ethylene glycol, propylene glycol, 1,3-butylene glycol, diglycerol, polyglycerol, diethylene glycol, polyethylene glycol, dipropylene glycol, polypropylene glycol, sorbitan, sorbitol, mannitol, xylitol, erythritol, trehalose and the like.

Of these water-soluble polyhydric alcohols, preferables are, for example, glycerol, diglycerol and polyglycerol.

An amount of the water-soluble polyhydric alcohol to be incorporated is 0.01–20% by weight, preferably 0.1–10% by weight. If it is less than 0.1%, dispersibility and re-dispersibility of the suspension may be decreased, while, if more than 20%, its viscosity may be increased, which leads to an unpleasant rough feeling in the mouth.

The inorganic powder as used herein is meant to be an inorganic compound containing one or more components selected from the group consisting of magnesium, aluminum, titanium and silicic acids.

As the inorganic compounds, there may be mentioned, for example, magnesium oxide, magnesium hydroxide, aluminum magnesium hydroxide, aluminum magnesium metasilicate, magnesium carbonate, magnesium chloride, magnesium sulfate, aluminum oxide, aluminum hydroxide gel, titanium oxide, light anhydrous silicic acid and the like, and they may be used alone or in combination with two or more thereof.

Particularly preferable inorganic compounds are titanium oxide, aluminum magnesium hydroxide, aluminum hydroxide gel and light anhydrous silicic acid alone or in the form of a mixture of two or more thereof.

The said sparingly water-soluble acidic drug may produce an unacceptably highly irritating action on the oropharyngeal mucous membrane, but incorporation of the inorganic powders may improve the stability of suspended particles after high-temperature sterilization and greatly decrease the irritative property of the drug. Thus, it is advantageous to incorporate the inorganic powders.

In the present invention, the suspending liquid preparation may have preferably a pH value of 2–5. The suspending liquid preparation with pH 2–5 may be prepared by using a buffer (e.g. citrate buffer). pH of 3–4 is particularly preferred.

In the invention, it is preferable to incorporate a high molecular compound not only for improving a sedimentation stability of suspended particles but also for further improving stability of suspended particles with lapse of time. As the high molecular compounds which may be incorporated, there may be mentioned, for example, xanthan gum, crystalline cellulose, vinyl carboxylate polymers, ethylcellulose, hydroxyethylcellulose, polyvinyl alcohol, polyvinyl pyrrolidone, alginic acid, dextrin, sodium hyaluronate, chondroitin sulfate and the like. These high molecular compounds may be used alone or in combination with two or more thereof. Of these high molecular compounds, preferably used are the compounds having a particularly low solubilizing ability such as xanthan gum, crystalline cellulose and the like.

In the pulverization step according to the invention, a rate of the sparingly water-soluble acidic drug (and the inorganic powder) is suitably 5–50% of the water to be applied. If it is lower than the said range, pulverization may be inferior, while, if higher than the said range, a viscosity of the material to be pulverized may be increased to provide insufficient pulverization. The sparingly water-soluble acidic drug (and the inorganic powder) thus pulverized is present in the form of fine particles and the suspended particle size is not more than 15 μm, 1–10 μm being particularly preferred.

The suspension of this invention can be prepared, for example, by mixing all components and pulverizing the sparingly water-soluble acidic drug (and the inorganic powder) to an average particle size of 1–15 μm by means of, for example, a pulverizer comprising a main shaft adapted to rotate in a casing and a plurality of layshafts adapted to revolve in relationship interlocked with the rotation of the main shaft, each of the layshafts being fitted with a multiplicity of annular grinding media.

A pulverizer to be used may preferably have, for example, an annular medium with an outer diameter of 25–45 mm and a thickness of several millimeters and a rotation number is in the range of 50–5000 rpm, depending upon the size of a pulverizer and others.

The inorganic powder may be also incorporated into the suspension after it is separately pulverized to 1–15 μm. Also, it is preferable to incorporate a high molecular compound into the suspension and then warm the resultant suspension to 50–60° C. in order to increase stability of the suspension with lapse of time.

In this invention, there may be incorporated other substance having a protecting action on the mucous membrane.

As membrane-protecting substances, there may be used sucralfate and other derivatives or calcium salt thereof, mucin, hydroxypropylmethylcellulose, acrylic acid and other natural and/or synthetic polymeric materials.

There may be incorporated into the suspension of this invention other active ingredients, for example, sodium copper chlorophyllin, azulene, allantoin, aluminum allantoinate, silicone oil, scopolia extract, cinnamon oil, clove oil, other crude drug components, gastrointestinal drugs such as atropine, scopolamine, ethyl aminobenzoate, etc., vitamins such as vitamin B1, B2 or B6, vitamin C, vitamin A, vitamin D, vitamin E, etc., calcium preparations such as calcium aspartate, calcium lactate, etc., other antipyretic analgesics, muscle relaxants, antispasmodics, antihistaminics, sympathomimetic drugs and the like as far as they would not adversely affect the effect of this invention.

Also, there may be further incorporated other substances generally employed in the art such as pharmacologically acceptable sweetening agents, pH adjusters, preservatives, perfumes, coloring agents and others.

As the sweetening agent, there may be mentioned, for example, lactose, sucrose, fructose, glucose, sorbitol, mannitol, erythritol, xylitol, trehalose, Stevia extract, and the like.

As the pH adjuster, there may be mentioned, for example, lactic acid, citric acid, malic acid, succinic acid, fumaric acid, tartaric acid, phosphoric acid and salts thereof and the like.

As the preservative, there may be mentioned, for example, parabens such as methyl p-oxybenzoate, ethyl p-oxybenzoate, propyl p-oxybenzoate, butyl p-oxybenzoate, etc., benzoic acid or salts thereof.

As the perfume, there may be mentioned, for example, fruit flavors such as orange, grapefruit, apple, lemon, lime, tangerine, citron, mandarin orange, summer orange, grape, strawberry, pineapple, banana, peach, melon, water melon, plum, cherry, pear, apricot, currant, Japanese apricot, mango, mangosteen, guava, raspberry, blueberry, etc., and other flavors such as green tea, black tea, cocoa, chocolate, coffee, almond, maple, vanilla, whiskey, brandy, rum, wine, liqueur, cocktail, mint, etc. They may be used alone or in the form of a mixed flavor composed of two or more thereof.

BEST MODE FOR CARRYING OUT THE INVENTION

This invention will be then explained more specifically by reference to the following Test Examples and Examples.

TEST EXAMPLE 1
Evaluation (1) of Surface Active Agents

A mixture of 450 mg of ibuprofen, surface active agent 0.05–0.1% by weight and 100 mg of citric acid was adjusted to pH 3 with 1N sodium hydroxide and treated by a homomixer at 8000 rpm for 20 minutes. Then, ibuprofen particles were sedimented by centrifugation, a supernatant was filtered through a 0.2 μm filter and a concentration of the dissolved ibuprofen was determined by HPLC method.

As is apparent from the results of Table 1, polyglycerol fatty acid esters were superior in maintaining a lower solubility of ibuprofen as compared with other surface active agents.

TABLE 1

Solubility of ibuprofen with surface active agents

| Surface active agent | Concentration (%) | Concentration of dissolved ibuprofen (μg/mL) |
| --- | --- | --- |
| TO10M* | 0.05 | 90.8 |
|  | 0.1 | 134.4 |
| Sucrose stearate | 0.05 | 44.7 |
|  | 0.1 | 72.6 |
| Decaglycerol monostearate | 0.05 | 28.6 |
|  | 0.1 | 29.0 |

*TO10M: Polyoxyethylene sorbitan monooleate (20 E.O.)

TEST EXAMPLE 2
Evaluation (2) of Surface Active Agents

A mixture of 450 mg of ibuprofen, surface active agent 0.1% by weight and 100 mg of citric acid was adjusted to pH 3 with 1N sodium hydroxide and treated by a homomixer at 8000 rpm for 20 minutes. Then, the products were stored at 65° C., 25° C. and 5° C. and stability of ibuprofen suspension was evaluated.

As is apparent from Table 2, polyglycerol fatty acid esters were superior in stability of the suspension with lapse of time.

TABLE 2

Influence upon stability of ibuprofen suspension by surface active agents

| | Concen- | Conditions for changes with lapse of time | | |
| --- | --- | --- | --- | --- |
| Surface active agent | tration (%) | 65° C. 1 week | 25° C. 1 month | 5° C. 1 month |
| TO10M* | 0.1 | X Floatings generated | X Floatings generated | X Floatings generated |
| HCO60** | 0.1 | X Floatings generated | X Floatings generated | X Floatings generated |
| Decaglycerol monostearate | 0.1 | ◯ No change | ◯ No change | ◯ No change |

*TO10M: Polyoxyethylene sorbitan monooleate (20 E.O.)
**HCO60: Polyoxyethylene hydrogenated castor oil

TEST EXAMPLE 3
Evaluation of Thickners

A mixture of 450 mg of ibuprofen, thickener 0.1–1.0% by weight and 100 mg of citric acid was adjusted to pH 3 with 1N sodium hydroxide and treated by a disperser at 1500 rpm for 20 minutes. Then, ibuprofen particles were sedimented by centrifugation, a supernatant was filtered through a 0.2 μm filter and a concentration of the dissolved ibuprofen was determined by HPLC method.

As is apparent from the results of Table 1, xanthan gum was superior in maintaining a lower solubility of ibuprofen as compared with other surface active agents.

TABLE 3

Effect of thickeners on ibuprofen solubility

| Thickener | Concentration (%) | Concentration of dissolved ibuprofen (μg/mL) |
| --- | --- | --- |
| CMC—Na* | 0.1 | 63.0 |
|  | 0.5 | 79.0 |
|  | 1.0 | 88.5 |
| Xanthan gum | 0.1 | 0 |
|  | 0.5 | 0 |
|  | 1.0 | 4.7 |

*CMC—Na: Sodium carboxymethylcellulose

TEST EXAMPLE 4
Evaluation of Pulverization Methods

A mixture of 60 g of ibuprofen, 12 g of surface active agent (polyglycerol monostearate), 50 g of glycerol and 200 g of 0.5% citrate buffer (pH 4) was treated at 1000 rpm for 10 minutes by means of Micros MIC-0 type mixer (Nara Kikai Seisakusho) and then diluted with said citrate buffer to 50 times. For comparison, 50-fold diluted ibuprofen with said citrate buffer, the surface active agent and glycerol were processed by means of pulverizing and dispersing apparatus recited in Table 4 (provided that the disperser was treated according to the method of Test Example 2 and the homomixer was according to the method of Test Example 1) and then particle size was measured by means of a particle size distribution meter (Microtrack Inc.).

TABLE 4

Ability of various processing apparatuses to pulverize ibuprofen

| Pulverizing and dispersing apparatus | Process condition | Particle size of ibuprofen (μm) Average particle size (particle size distribution) |
| --- | --- | --- |
| Unprocessed | — | 37 (12.8–66.8) |
| Disperser | 1500 rpm, 20 min. | 41 (16.7–72.3) |
| Homomixer | 8000 rpm, 20 min. | 36 (14.1–62.5) |
| Colloid mill | 12 hrs. | Melted |
| Micros (Micronizer) | 650 rpm, 10 min. | 3 (1.3–7.3) |

As is shown in Table 4, a particle size of ibuprofen was micronized to 1.3–7.3 μm with no ibuprofen floatings being observed according to the processing by Micros. Pulverization was not feasible by means of other apparatuses. By using a dry colloid mill, ibuprofen was melted and its pulverization was difficult.

TEST EXAMPLE 5
Dissolution Test

In accordance with the Japanese Pharmacopoeia, the dissolution test was carried out using the Eluting Solution I at 37° C. and 100 rpm according to a paddle method and ibuprofen was determined by means of HPLC method.

TABLE 5

Test results of ibuprofen dissolution

| Processing apparatus | Average particle size (μm) | Dissolution time | | | |
|---|---|---|---|---|---|
| | | 0 min. | 5 min. | 10 min. | 30 min. |
| Micros | 3 | 0% | 93.2% | 98.2% | 100% |
| Homomixer | 36 | 0% | 41.3% | 59.0% | 83.7% |

The ibuprofen suspension pulverized by means of Micros (average particle size 3 μm) had a remarkably higher dissolution rate than that of the ibuprofen suspension pulverized by means of a homomixer (average particle size 36 μm).

TEST EXAMPLE 6

Evaluation of Stability Against High-temperature Sterilization

TABLE 6

Examples of Formulations (mg/30 ml)

| | Comp. Ex. 1 | Ex. 1 | Ex. 2 | Ex. 3 | Ex. 4 | Ex. 5 |
|---|---|---|---|---|---|---|
| Ibuprofen | 150 | 150 | 150 | 150 | 150 | 150 |
| Polyglycerol fatty acid ester | 15 | 15 | 15 | 15 | 15 | 15 |
| Glycerol | 2 | 2 | 2 | 2 | 2 | 2 |
| Aluminum magnesium hydroxide | 0 | 80 | 0 | 0 | 0 | 80 |
| Aluminum magnesium metasilicate | 0 | 0 | 150 | 0 | 0 | 0 |
| Aluminum hydroxide gel | 0 | 0 | 0 | 50 | 0 | 50 |
| Magnesium hydroxide | 0 | 0 | 0 | 0 | 80 | 0 |
| Titanium oxide | 0 | 0 | 0 | 0 | 100 | 100 |
| Xanthan gum | 0.6 | 0.6 | 0.6 | 0.6 | 0.6 | 0.6 |
| Citric acid | 500 | 500 | 500 | 500 | 500 | 500 |
| Sodium hydroxide | q.s. | q.s. | q.s. | q.s. | q.s. | q.s. |
| pH | 4 | 4 | 4 | 4 | 4 | 4 |
| Floating oily material | X | ○ | ○ | ○ | ○ | ○ |
| Crystal aggregation | X | ○ | ○ | ○ | ○ | ○ |

[Evaluation method]

Floating oily materials were visually determined for the degree of oily droplets floating over the liquid surface and expressed as accepted (○) when the oily materials were not observed or hardly observed, and as rejected (X) when the oily materials were observed or noticeably observed. The degree of crystal aggregation was visually determined for the size of crystals as sedimented and expressed as accepted (○) when the size of crystals remained unchanged or hardly changed, and as rejected (X) when it was increased or remarkably increased.

In reference to the formulations as shown in Table 6, ibuprofen was pulverized with the surface active agent under the Micros processing condition as in Test Example 4 and then blended with pulverized inorganic powders (which may be those pulverized by means of Micros) and xanthan gum and then diluted to a predetermined amount. Thereafter, the mixture was heated to 95° C. for 5 minutes and the floating of ibuprofen oily material onto the interface (liquid-vapor) and the aggregation degree of ibuprofen crystal after cooling were investigated.

If inorganic powders were blended, ibuprofen oily material onto the interface was not observed and a large mass of ibuprofen was not found even after cooling.

TEST EXAMPLE 7

Evaluation of Irritative Property

Each of the formulations in terms of Comparative Example and Examples shown in Table 6 was orally given in a single dose and evaluated. Evaluation was performed with 6 healthy adult volunteers. Sensory test was accomplished by expressing an irritating level to throat numerically on the basis of the following standard and comparing numerical values each other.

From the result of this test, it was seen that irritating property was lessened by blending these inorganic powders.

TABLE 7

Results of sensory evaluation (Average values)

| | Comp. Ex. 1 | Ex. 1 | Ex. 2 | Ex. 3 | Ex. 4 | Ex. 5 |
|---|---|---|---|---|---|---|
| Irritative feeling to throat | 3.3 | 0.7 | 1.3 | 0.7 | 1.2 | 0 |

[Standard for sensory evaluation]:
0: No irritation to throat felt
1: Irritation to throat hardly felt
2: Irritation to throat faintly felt
3: Irritation to throat felt
4: Irritation to throat intensely felt

EXAMPLE 6

A mixture of 60 g of ibuprofen, 12 g of surface active agent (polyglycerol monostearate), 50 g of glycerol and 200 g of 0.5% citrate buffer (pH 3) was processed at 1000 rpm for 10 minutes by means of Micros MIC-0 type mixer (Nara Kikai Seisakusho) and then diluted with said citrate buffer to 50 times. Xanthan gum was added as a thickener, the mixture was uniformly dispersed and then another drug dihydrocodein phosphate was added. The whole mixture was uniformly dispersed by means of a disperser, a total amount was adjusted to 100% by adding purified water and then heated at a temperature of from 55 to 65° C. for 20 minutes.

| (per 30 ml) | |
|---|---|
| Ibuprofen | 144 mg |
| Dihydrocodein phosphate | 8 mg |
| Polyglycerol monostearate | 28.8 mg |
| Glycerol | 120 mg |
| Xanthan gum | 90 mg |
| Sweetening agent | 10000 mg |
| 0.5% Citrate buffer (pH 3) | 300 mg |
| Antiseptic | q.s. |
| Purified water | q.s. |

EXAMPLE 7

Following the same procedure as described in Example 6, there was obtained the suspension containing the following components.

| (per 30 ml) | |
|---|---|
| Ibuprofen | 144 mg |
| Acetaminophen | 200 mg |
| Chlorpheniramine maleate | 2.5 mg |
| Methylephedrine hydrochloride | 20 mg |

-continued

| (per 30 ml) | |
|---|---|
| Polyglycerol monostearate | 28.8 mg |
| Glycerol | 60 mg |
| Xanthan gum | 60 mg |
| Sweetening agent | 10000 mg |
| 0.5% Citrate buffer (pH 4.5) | 300 mg |
| Antiseptic | q.s. |
| Purified water | q.s. |

EXAMPLE 8

Following the same procedure as described in Example 6, there was obtained the suspension containing the following components.

| (per 30 ml) | |
|---|---|
| Ibuprofen | 144 mg |
| Dihydrocodein phosphate | 8 mg |
| Chlorpheniramine maleate | 2.5 mg |
| dl-Methylephedrine hydrochloride | 20 mg |
| Lysozyme chloride | 30 mg (titer) |
| Polyglycerol monostearate | 28.8 mg |
| Glycerol | 60 mg |
| Xanthan gum | 60 mg |
| Sweetening agent | 10000 mg |
| 0.5% Citrate buffer (pH 4) | 300 mg |
| Antiseptic | q.s. |
| Purified water | q.s. |

EXAMPLE 9

Following the same procedure as described in Example 6, there was obtained the suspension containing the following components.

| (per 30 ml) | |
|---|---|
| Ibuprofen | 144 mg |
| Dihydrocodein phosphate | 8 mg |
| Bromhexine hydrochloride | 12 mg |
| Chlorpheniramine maleate | 2.5 mg |
| dl-Methylephedrine hydrochloride | 20 mg |
| Lysozyme chloride | 30 mg (titer) |
| Polyglycerol monostearate | 28.8 mg |
| Glycerol | 60 mg |
| Xanthan gum | 60 mg |
| Sweetening agent | 10000 mg |
| 0.5% Citrate buffer (pH 4) | 300 mg |
| Antiseptic | q.s. |
| Purified water | q.s. |

EXAMPLE 10

Following the same procedure as described in Example 6, there was obtained the suspension containing the following components.

| (per 30 ml) | |
|---|---|
| Ibuprofen | 144 mg |
| Anhydrous caffeine | 16.6 mg |
| Glycyrrhiza extract | 166.7 mg |
| Cinnamon extract | 100 mg |
| Ginger extract | 75 mg |
| Polyglycerol monostearate | 28.8 mg |
| Glycerol | 60 mg |
| Xanthan gum | 60 mg |
| Sweetening agent | 10000 mg |
| 0.5% Citrate buffer (pH 3.5) | 300 mg |
| Antiseptic | q.s. |
| Purified water | q.s. |

EXAMPLE 11

Following the same procedure as described in Example 6, there was obtained the suspension containing the following components.

| (per 30 ml) | |
|---|---|
| Ibuprofen | 144 mg |
| Anhydrous caffeine | 25 mg |
| Dihydrocodein phosphate | 8 mg |
| Bromhexine hydrochloride | 12 mg |
| Chlorpheniramine maleate | 2.5 mg |
| dl-Methylephedrine hydrochloride | 20 mg |
| Lysozyme chloride | 30 mg (titer) |
| Ginseng extract | 30 mg |
| Polyglycerol monostearate | 28.8 mg |
| Glycerol | 60 mg |
| Xanthan gum | 60 mg |
| Aluminum magnesium hydroxide | 100 mg |
| Titanium oxide | 100 mg |
| Sweetening agent | 10000 mg |
| 0.5% Citrate buffer (pH 4) | 300 mg |
| Antiseptic | q.s. |
| Purified water | q.s. |

EXAMPLE 12

Following the same procedure as described in Example 6, there was obtained the suspension containing the following components.

| (per 30 ml) | |
|---|---|
| Ibuprofen | 100 mg |
| Acetaminophen | 200 mg |
| Anhydrous caffeine | 25 mg |
| Dihydrocodein phosphate | 8 mg |
| Bromhexine hydrochloride | 12 mg |
| Chlorpheniramine maleate | 2.5 mg |
| dl-Methylephedrine hydrochloride | 20 mg |
| Glycyrrhiza extract | 150 mg |
| Polyglycerol monostearate | 28.8 mg |
| Glycerol | 60 mg |
| 1-Menthol | 1 mg |
| Xanthan gum | 60 mg |
| Sweetening agent | 10000 mg |
| 0.5% Citrate buffer (pH 3.5) | 300 mg |
| Antiseptic | q.s. |
| Purified water | q.s. |

EXAMPLE 13

Following the same procedure as described in Example 6, there was obtained the suspension containing the following components.

| (per 30 ml) | |
|---|---|
| Ibuprofen | 100 mg |
| Acetaminophen | 200 mg |
| Anhydrous caffeine | 25 mg |
| Dihydrocodein phosphate | 8 mg |
| Ambroxol hydrochloride | 15 mg |
| Chlorpheniramine maleate | 2.5 mg |
| Methylephedrine hydrochloride | 20 mg |
| dl-Methylephedrine hydrochloride | 20 mg |
| Lysozyme chloride | 30 mg (titer) |
| Glycyrrhiza extract | 150 mg |
| Polyglycerol monostearate | 28.8 mg |
| Glycerol | 60 mg |
| 1-Menthol | 1 mg |
| Xanthan gum | 60 mg |
| Sweetening agent | 10000 mg |
| 0.5% Citrate buffer (pH 4) | 300 mg |
| Antiseptic | q.s. |
| Purified water | q.s. |

EXAMPLE 14

Following the same procedure as described in Example 6, there was obtained the suspension containing the following components.

| (per 30 ml) | |
|---|---|
| Ibuprofen | 144 mg |
| Anhydrous caffeine | 16.6 mg |
| Glycyrrhiza extract | 166.7 mg |
| Cinnamon extract | 100 mg |
| Ginger extract | 75 mg |
| Polyglycerol monostearate | 28.8 mg |
| Glycerol | 60 mg |
| Xanthan gum | 60 mg |
| Aluminum magnesium hydroxide | 80 mg |
| Aluminum hydroxide gel | 50 mg |
| Titanium oxide | 100 mg |
| Sweetening agent | 10000 mg |
| 0.5% Citrate buffer (pH 3) | 300 mg |
| Antiseptic | q.s. |
| Purified water | q.s. |

Industrial Applicability

According to this invention, there can be provided a suspension of a sparingly water-soluble acidic drug (especially, ibuprofen and the like) which has excellent thermal stability and dispersion stability over a prolonged period of time and highly dissolvable, and which does not need to be redispersed by vigorous shaking just before oral administeration because no tight sedimentation of suspended particles to the bottom of a vessel occurs. Moreover, the present suspension can be subjected to a high-temperature sterilization and can be prepared so as not to give an unpleasant rough feeling in the mouth.

Furthermore, according to the process for the preparation of this invention, there may be simply and easily prepared a suspension having superior properties.

What is claimed is:

1. A suspension which comprises a sparingly water-soluble acidic drug whose average particle size is from 1 to 15 µm, a polyglycerol fatty acid ester, a water-soluble polyhydric alcohol and water, said suspension having a pH value of 2–5.

2. A suspension which comprises a sparingly water-soluble acidic drug whose average particle size is from 1 to 15 µm, an inorganic powder whose average particle size is from 1 to 15 µm, a polyglycerol fatty acid ester, a water-soluble polyhydric alcohol and water, said suspension having a pH value of 2–5.

3. The suspension as claimed in claim 2 wherein said sparingly water-soluble acidic drug is ibuprofen.

4. The suspension as claimed in claim 1 wherein said inorganic powder is at least one inorganic compound selected from the group consisting of magnesium compounds, aluminum compounds, titanium compounds and silicic acid compounds.

5. The suspension as claimed in claim 1 further comprising at least one of xanthan gum and crystalline cellulose.

6. The suspension as claimed in claim 1 wherein it is subjected to a heat treatment at 50–60°.

7. A process for the preparation of a suspension of a sparingly water-soluble acidic drug whose average particle size is from 1 to 15 µm, which comprises pulverizing and dispersing a sparingly water-soluble acidic drug, a polyglycerol fatty acid ester, a water-soluble polyhydric alcohol and water by means of a pulverizer comprising a main shaft adapted to rotate in a casing and a plurality of layshafts adapted to revolve in relationship interlocked with the rotation of the main shaft, each of the layshafts being fitted with a multiplicity of annular grinding media.

8. The suspension as claimed in claim 2 wherein said sparingly water-soluble acidic drug is ibuprofen.

9. The suspension as claimed in claim 2 wherein said inorganic powder is at least one inorganic compound selected from the group consisting of magnesium compounds, aluminum compounds, titanium compounds and silicic acid compounds.

10. The suspension as claimed in claim 3 wherein said inorganic powder is at least one inorganic compound selected from the group consisting of magnesium compounds, aluminum compounds, titanium compounds and silicic acid compounds.

11. The suspension as claimed in claim 2 further comprising at least one of xanthan gum and crystalline cellulose.

12. The suspension as claimed in claim 3 further comprising at least one of xanthan gum and crystalline cellulose.

13. The suspension as claimed in claim 4 further comprising at least one of xanthan gum and crystalline cellulose.

14. The suspension as claimed in claim 2 wherein it is subjected to a heat treatment at 50–60°.

15. The suspension as claimed in claim 3 wherein it is subjected to a heat treatment at 50–60°.

16. The suspension as claimed in claim 4 wherein it is subjected to a heat treatment at 50–60°.

17. The suspension as claimed in claim 5 wherein it is subjected to a heat treatment at 50–60°.

* * * * *